United States Patent [19]

Polgár et al.

[11] Patent Number: 5,097,031
[45] Date of Patent: Mar. 17, 1992

[54] STEROSELECTIVE HYDROGENATION PROCESS

[75] Inventors: István Polgár; József Foldesi; János Kiss; Piroska Major née Forstner; Károly Molnár; András Sugár; Tamás Szén; Katalin Balogh née Nemes, all of Budapest, Hungary

[73] Assignee: Richter Gedeon Vegyeszeti Gyar R.T., Budapest, Hungary

[21] Appl. No.: 542,168

[22] Filed: Jun. 22, 1990

[30] Foreign Application Priority Data

Jun. 27, 1989 [HU] Hungary .................. 3225/89

[51] Int. Cl.$^5$ .................................. C07D 457/02
[52] U.S. Cl. ............................ 546/67; 546/68; 546/69
[58] Field of Search ................... 546/67, 68, 69

[56] References Cited

U.S. PATENT DOCUMENTS 4,731,367 3/1988 Sauer et al. .............. 546/67

FOREIGN PATENT DOCUMENTS 658058 10/1986 Switzerland .............. 546/67

OTHER PUBLICATIONS

Pharmazie, 39, pp. 537–538 (1984).
Pharmazie 28, pp. 486–487 (1973).
Rylander, P. N. Catalytic Hydrogenation in Organic Syntheses, pp. 51 and 285–290 (1979).
English Translation of Stoll, A. et al, Helv. Chim. Acta. 29, 635–637 and 646–647 (1946) (Original Cited by the Examiner).
Rylander, P. N., Catalytic Hydrogenation over Platinum Metals pp. 440–443 (1967).
Rylander, P. N., Catalytic Hydrogenation in Organic Syntheses pp. 31–32 (1979).
English Translation of Stoll, A. et al, Helv. Chim. Acta 26, 2070–2074, (1943).
Saburo Yamatodani et al, Bull Org. Chem. Soc. Japan. vol. 20, pp. 95–96 (1956).
B. Berde et al, Ergot Alkaloids and Related Compounds p. 57 (1978).
Mago-Karacsony et al, CA 92-42218g (1980).
W. Jacobs et al, J. Biol. Chem. 113, 767–778 (1936).
A. Stoll et al, Helv. Chim Acta, 29, 635–653 (1946).
A. Stoll et al, Helv. Chim. Acta, 26, 2070–2081 (1943).
Craig, J. Biol. Chem. 108,595 (1935).
J. Biol. Chem. 115, 227 (1936).

Primary Examiner—Cecilia Shen
Attorney, Agent, or Firm—Herbert Dubno; Jonathan Myers

[57] ABSTRACT

The invention relates to a novel stereoselective process for the preparation of dihdyrolysergol from lysergol by hydrogenation in the presence of solvent and palladium catalyst applied on a carrier, which comprises hydrogenating lysergol in the presence of one or more aprotic solvent(s) containing tertiary nitrogen atom(s) and a palladium catalyst applied on activated carbon, and recovering the product obtained from the reaction mixture in a known manner.

2 Claims, No Drawings

STEREOSELECTIVE HYDROGENATION PROCESS

This invention relates to a stereoselective hydrogenation process for the preparation of dihydrolysergol from lysergol in the presence of a solvent and a palladium catalyst applied on a carrier.

10α-ergolines are starting substances for the preparation of therapeutically very valuable compounds of specific action. From 10α-ergolines dihydrolysergol (chemically 8β-hydroxymethyl-6-methylergoline), showing also an own therapeutically useful (cytostatic) effect, is of outstanding importance (E. Eich et al., Planta Med. 1986. 290).

Dihydrolysergol and its isomers have been prepared first by W. A. Jacobs and L. C. Craig [J. Biol. Chem. 108, 595 (1935)] by the reduction of ergotinine with sodium in butanol. Later, the same authors obtained a similar mixture of isomers from dihydrolysergic acid methyl ester in an analogous reaction [J. Biol. Chem. 115, 227 (1936)].

Stoll et al. prepared dihydrolysergol in a yield of 74% by reducing dihydrolysergic acid methyl ester with lithium aluminum hydride.

The literature references cited above contain valuable data on the physical and chemical characteristics (melting point, optical rotation) of dihydrolysergol.

A practically important process for selective hydrogenation of lysergol was described in the Hungarian patent specification No. 174,577, wherein lysergol was hydrogenated in an alkanolic medium by using a particular palladium catalyst applied on an aluminum oxide carrier. The hydrogenation was carried out in a very dilute solution of about 1% concentration in the presence of a high amount (being equal to the weight of lysergol to be hydrogenated) of catalyst, and a yield of 85% is achieved.

The drawback of this process consists in the occurrance of side reactions. R. Voigt and P. Zier [Pharmazie 28, 486 (1973)] reported on the possible side products of hydrogenating reactions performed by using palladium catalyst in the presence of a protic solvent.

K. Mayer and E. Eich prepared dihydrolysergol in a yield of 90% starting from lysergol by using the transfer hydrogenation process with Raney nickel catalyst in a solvent mixture of dioxane and alkanol. This hydrogenation was similarly performed in a very dilute solution, in the presence of a high amount of the catalyst (being present in a 3-fold weight calculated for the lysergol to be hydrogenated) [Pharmazie 39, 537 (1984)].

A common disadvantage of the processes known from the literature consists therein that the hydrogenation is carried out in a very dilute solution (of about 1% concentration); a further drawback resides in that a very high amount of catalyst calculated for the unit of the substance to be hydrogenated is used. An additional drawback of the processes known in the art is that side reactions occur in the course of hydrogenation and therefore the crude product obtained from the reaction mixture is to be purified by recrystallization.

The aim was set to eliminate the above disadvantages of the known methods and, above all, to improve the selectivity of the hydrogenation, as well as to develop a hydrogenation process preferable from the point of view of technical and economical conditions of a commercial scale production.

Surprisingly, it has now been found that dihydrolysergol can be prepared with a practically quantitative yield and of a very high purity; simultaneously, the concentration of the substance to be hydrogenated can be increased in the solvent by one order; and the amount of catalyst can be decreased by two orders (i.e. the hydrogenation is carried out in a solution containing 10% of lysergol in the presence of 2% of catalyst) if the catalytic hydrogenation of lysergol is carried out in an aprotic organic solvent medium containing tertiary nitrogen atom(s) and using palladium catalyst applied on activated carbon carrier.

The above process is all the more surprising as the hydrogenation can be realized in an aprotic solvent containing tertiary nitrogen(s) (e.g. in N,N-dimethylformamide and/or pyridine) while the amount of the catalyst is simultaneously decreased. On the other side it is known that the efficiency of the catalyst is moderated by solvents containing tertiary nitrogen; and even pronouncedly decreased by solvents of amine type. On the contrary to this the activity of palladium catalysts is significantly increased by alkanols or carboxylic acids. Thus, in the processes of the prior art alkanols are used as solvents, however, even under such conditions a very high excess of the catalyst must be used. Therefore, with full knowledge of the prior art processes, it is an unexpected effect that the amount of the catalyst can be diminished by two orders, the reaction can be carried out in a substantially more concentrated solution and in addition, the reaction proceeds very rapidly and quantitatively with a complete selectivity when the hydrogenation is carried out in an aprotic solvent containing tertiary nitrogen.

Thus, the present invention relates to a stereoselective process for preparing dihydrolysergol from lysergol by hydrogenation in the presence of a solvent and a palladium catalyst applied on a carrier, which comprises hydrogenating lysergol in the presence of one or more aprotic solvent(s) containing tertiary nitrogen atom(s) and a palladium catalyst applied on activated carbon and then recovering the product obtained from the reaction mixture in a manner known per se.

According to an embodiment of the present invention lysergol is dissolved in one or more aprotic solvent(s) containing tertiary nitrogen atom(s) and after adding the catalyst the mixture is hydrogenated by using gaseous hydrogen under atmospheric pressure or a low overpressure until complete saturation. Preferable solvents are N,N-dimethylformamide, pyridine or their mixture.

As catalyst 5 to 10% of palladium applied on activated carbon as carrier is used; any of the commercially available catalysts commonly used is suitable for this purpose.

The hydrogenation is suitably carried out at an elevated temperature, preferably at a temperature of between 40° C. and the boiling point of the reaction mixture. It was found that 60° C. is the most preferred reaction temperature.

The hydrogenation may be performed under atmospheric pressure, however, particularly on an industrial scale, a pressure of 2 to 5 bars is conveniently employed to shorten the reaction time and thereby to increase the production capacity.

The completion of the reaction can be observed by using a convenient analytical examination such as chromatography. In general the reaction lasts 3 to 4 hours.

After the reaction is completed the catalyst is filtered off, then the product is crystallized by adding water to the reaction mixture and the crystals are isolated.

The more important advantages of the process according to the invention can be summarized as follows.

1. The selectivity of the hydrogenating reaction is significantly improved whereas the side reactions are suppressed. Thus, the yield is significantly increased and a product of substantially higher purity is obtained in comparison to those derived from processes of the prior art.

2. The concentration of the substance to be hydrogenated is increased by one order thus, the process of the invention is very useful for an industrial implementation.

3. The amount of the catalyst required is diminished by two orders therefore, the process of the invention is very advantageous from both technical and economical aspects.

The process according to the invention is illustrated in detail by the following non limiting Examples.

EXAMPLE 1

0.3 g of a catalyst containing 10% of palladium on activated carbon is added to a solution containing 13 g (0.0511 mol) of lysergol in a mixture of 300 ml of N,N-dimethylformamide and 30 ml of pyridine, then the mixture is hydrogenated at 60° C. under atmospheric pressure. The hydrogenation is continued until disappearance of the last traces of the starting substance (what is controlled by chromatographic method). The hydrogenation lasts about 4 hours.

After the reaction was completed the catalyst is filtered off and 3000 ml of water is added to the filtrate, then it is cooled to 20° C. and stirred for one hour. The product is filtered and dried to obtain 12.5 g (0.0488 mol); 95.4% yield) of dihydrolysergol, m.p.: 288° C. (with decomposition) with a specific rotation of $-95°$ (c=0.5, pyridine).

EXAMPLE 2

0.2 g of a catalyst containing 10% of palladium on activated carbon is added to a solution of 13 g (0.0511 mol) of lysergol in a mixture of 125 ml of N,N-dimethylformamide and 5 ml of pyridine, then the mixture is hydrogenated at 60° C. under a pressure of 5 bar. The hydrogenation lasts about 3 hours (as detected by chromatographic method).

After the reaction was completed the catalyst is filtered off and 2000 ml of water is added to the filtrate, then it is cooled to 5° C. and stirred for 2 hours. The product is filtered and dried to obtain 12.9 g (0.0503 mol; 98.5% yield) of dihydrolysergol, m.p.: 288° C. (with decomposition) with a specific rotation of $-95°$ (c=0.5, pyridine).

We claim:

1. A stereoselective process for the preparation of dihydrolysergol from lysergol which comprises the steps of:
   (a) catalytically hydrogenating under a pressure of 1 to 5 bar, a reaction mixture comprising lysergol and least one aprotic solvent containing a tertiary nitrogen a solvent mixture of N,N-dimethylformamide and pyridine and a 5 to 10% palladium catalyst applied on activated carbon, at a temperature between 40° C. and the boiling point of the reaction mixture, to form dihydrolysergol; and
   (b) removing the dihydrolysergol from the reaction mixture.

2. The stereoselective process for the preparation of dihydrolysergol defined in claim 1 wherein the amount of the 5 To 10% palladium catalyst applied on activated carbon is diminished by 2 orders of magnitude with respect to the amount of said catalyst employed in the prior art hydrogenation processes.

* * * * *